United States Patent [19]

Röhlcke

[11] 4,279,593
[45] Jul. 21, 1981

[54] WIRE SUPPORTING MEANS FOR ORTHODONTIC PURPOSES

[76] Inventor: Friedrich-Wilhelm Röhlcke, Uferstrasse 23, D-7531 Kämpfelbach-Bilfingen, Fed. Rep. of Germany

[21] Appl. No.: 114,716

[22] Filed: Jan. 23, 1980

[30] Foreign Application Priority Data

Feb. 1, 1979 [DE] Fed. Rep. of Germany ....... 2903768

[51] Int. Cl.³ ............................................. A61C 7/00
[52] U.S. Cl. ...................................................... 433/8
[58] Field of Search ............................. 433/10, 11, 9, 8

[56] References Cited

U.S. PATENT DOCUMENTS

| | | | |
|---|---|---|---|
| 3,959,880 | 6/1976 | Andrews | 433/11 |
| 4,023,274 | 5/1977 | Wallshein | 433/11 |

Primary Examiner—Robert Peshock
Attorney, Agent, or Firm—Shenier & O'Connor

[57] ABSTRACT

An orthodontic wire support identification member for attachment to an orthodontic wire support having an attachment base incorporating a body in which at least one wire accomodating channel is provided, in which said identification member is releasably attached to the body for removal after the wire support is mounted on a tooth so that the member facilitates identification of different types of wire supporting brackets, the identification member being constructed to cover the channel when in position on said body.

9 Claims, 6 Drawing Figures

U.S. Patent    Jul. 21, 1981    4,279,593
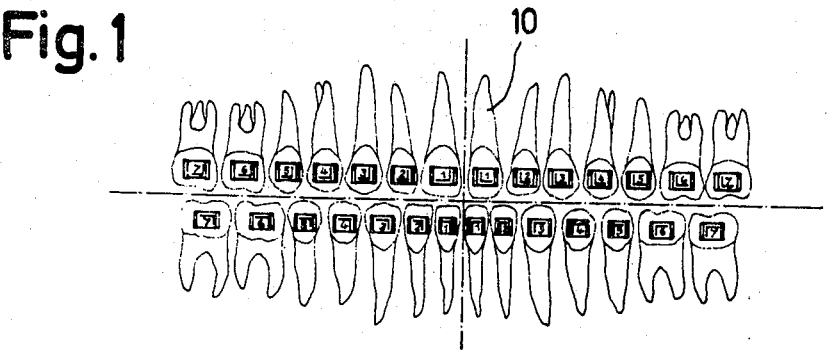
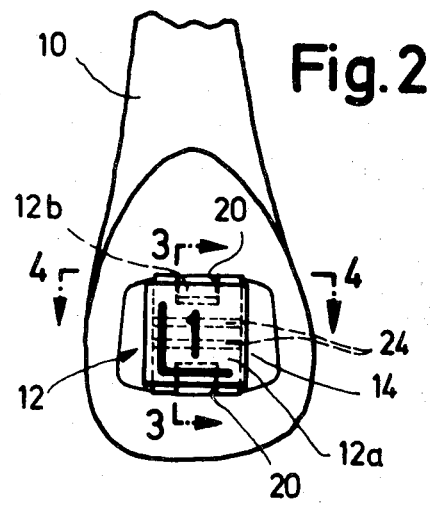
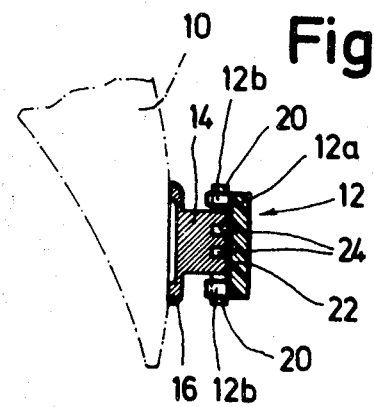
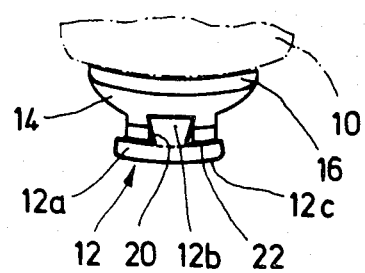
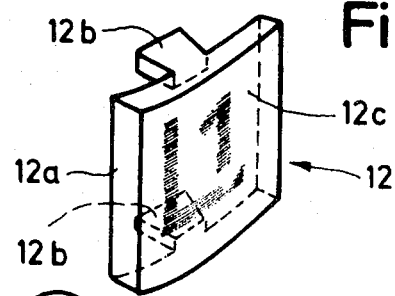
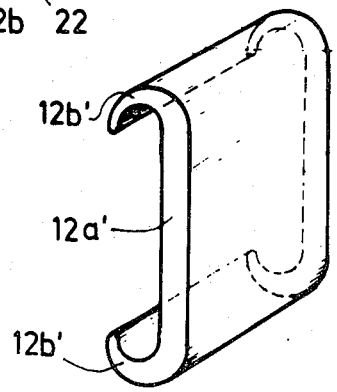

WIRE SUPPORTING MEANS FOR ORTHODONTIC PURPOSES

The invention relates to a wire supporting means for attachment to a tooth for orthodontic purposes comprising an attachment base and at least one recess for accommodating a wire, more particularly, a so-called bracket or a Buccal tube. Such wire supporting or wire guiding means are either fastened to a steel band, which, in turn, is fitted to a tooth, or the wire supporting means are adhered directly to a tooth using a suitable attachment base.

The relatively new so-called "Straight Wire Technique" requires a specially shaped wire supporting means for each tooth, which means that 28 different kinds of brackets or Buccal tubes must be available for one orthodontic treatment. Since the wire supporting means in question are relatively small, it is not only difficult for the person fitting the wire supporting means to the teeth to fasten to the respective tooth the proper wire supporting means for this type of tooth, but also extremely troublesome to arrange the various wire supporting members correctly in an assortment box, particularly if the wire supporting means have become mixed up during transportation.

A further problem is that when the bands carrying the wire supporting means are adhered or cemented to the teeth or the wire supporting means are directly fastened to the teeth, excessive cement must at all costs be prevented from getting into the recesses in the wire supporting means serving to hold or guide the wires, which further increases the need for care to be taken.

Accordingly, the object underlying the invention is to so improve the known wire supporting means of the aforementioned kind that they are simpler to work with. In accordance with the invention, this is to be attained in the form of a marking member releasably attached to the wire supporting means. Such a marking member enables each wire supporting means to be designated in the simplest manner, for example, by a corresponding inscription on the marking member and/or a corresponding coloring and/or a corresponding shape of the marking member, which makes the different types of wire supporting means easily distinguishable. At the same time, the marking member attached to a wire supporting means in accordance with the invention furnishes a simple way of preventing the recess provided in a wire supporting means for accommodation of a wire from becoming clogged with adhesive or cement. To this end, it is preferable that the marking member be so constructed that it covers or fills up the recess. After the wire supporting means is fitted on the tooth, the marking member is then removed so that the recess is easily accessible again.

The marking member could, in fact, be attached to the wire supporting means from either side. However, in order to ensure that the marking member remains on the wire supporting means while it is being fitted on the tooth without making handling of the wire supporting means difficult, it is recommended that the marking member be mounted on the side of the wire supporting means that faces away from the attachment base.

A preferred embodiment of the invention includes a marking member comprising a plate extending approximately parallel to the attachment base and having at least one integral holding portion to be mounted on or inserted in the wire supporting means. The plate provides adequate space for designation of the marking member and at the same time constitutes a good gripping point for removal of the marking member from the actual wire supporting means after attachment of the latter to the tooth.

The marking members according to the invention are simple and inexpensive to manufacture, particularly if they are made of plastic, since in that case cheap plastic injection molded parts are required. Further features, details and advantages of the invention are apparent from the enclosed claims and/or the following description and the accompanying drawings of two preferred embodiments of a wire supporting means and marking member in accordance with the invention.

FIG. 1 depicts the conventional international tooth schema, in which each tooth is provided with a so-called bracket with a marking member.

FIG. 2 is a side view of part of a tooth after a bracket with a marking member mounted thereon has been fitted.

FIG. 3 is a section taken along line 3—3 of FIG. 2, with the tooth merely indicated in dot-and-dash lines.

FIG. 4 is a section along line 4—4 of FIG. 2, with the tooth likewise merely indicated in dot-and-dash lines.

FIG. 5 is a perspective illustration of the marking member shown in FIGS. 2 to 4.

FIG. 6 is a perspective illustration of a second embodiment of the marking member.

The tooth designated 10 in FIGS. 1 and 2 is fitted with a bracket 14 which has a marking or tooth identification member 12 mounted thereon and is fastened directly to the tooth with the help of a so-called wire retention base 16. Such a wire retention base takes the form of a small curved metal plate, with the side facing the tooth having a suitable structure for direct attachment to the tooth surface with the aid of a cement. The likewise metal bracket 14 is welded to this small plate, which is not shown in further detail in FIGS. 3 and 4.

The bracket 14 comprises two grooves 20, namely one at the top and one at the bottom, extending downwardly and upwardly, respectively. At its front side 22 facing away from the base 16, the bracket 14 is provided with wire guiding slots 24 for insertion of the wires for correction of the tooth position.

The marking member 12, which is already positioned on the bracket, when supplied, consists essentially of a plate 12a, with two projections 12b of dovetail configuration when viewed from above, molded to its rear side, namely one at the top and one at the bottom. These projections extend through and beyond the grooves 20 of the bracket 14 and thus secure the marking member to the bracket, as is shown in FIG. 4. Accordingly, a special feature of the marking member according to the invention is that the length of the projections exceeds the length of the grooves 20 and that the width of the projections behind the grooves is larger, so that the marking members can only be removed from the brackets by force.

As indicated in FIGS. 1, 2 and 5, the front side 12c of the marking tooth identification member may be provided with a designation to mark or identify the tooth on which the respective bracket is to be fitted. The designation may, however, also be in the form of a corresponding shape or color of the marking member.

In the variant of the marking member according to the invention, as illustrated in FIG. 6, the projections 12b have been replaced by holding portions 12b' which embrace the upper and lower edges of the bracket 14.

This enables positioning of the marking member on the bracket, for example, from the side.

It is claimed:

1. An orthodontic wire support identification member for attachment to an orthodontic wire support, comprising a body, an attachment base on which said body is provided, and at least one channel in said body for accommodating a wire, characterized by said wire support identification member being releaseably attached to said body for removal after mounting of the orthodontic wire support on a tooth whereby said wire support identification member facilitates identification of different types of wire supporting wire supports, said identification member covering said channel when in position on said body.

2. An identification member as defined in claim 1, characterized in that said identification member (12) is disposed on the side of said wire support (14) that faces away from said attachment base (16).

3. An identification member as defined claim 1, characterized in that said identification member (12) comprises a plate (12a) extending approximately parallel to said attachment base (16) and having at least one integral holding portion (12b) to be mounted on said wire support (14).

4. An identification member as defined in claim 3, characterized in that one integral holding portion (12b) insertable in a correspondingly shaped groove (20) of said wire support (14) is provided on each of two opposite sides of said plate (12a).

5. An identification member as defined in claim 3 or 4, characterized in that said holding portion (12b) is of dovetail configuration and is positively held at said wire support (14).

6. An identification member as defined in claim 3, characterized in that one integral holding portion (12b') engaging over the adjacent side edge of said bracket (14) and preferably extending over the entire length of said side edge is provided on each of two opposite sides of said plate (12a').

7. An identification member as defined claim 1, characterized in that said identification member (12) is made of plastic.

8. An identification member as defined in claim 1, characterized in that said plate (12a) is approximately as large as, and said plate is at least as large as said wire support (14).

9. An identification member as defined in claim 1, characterized in that said identification member (12) comprises a plate (12a) extending approximately parallel to said attachment base (16) and having at least one integral holding portion (12b) to be inserted in said wire support (14).

* * * * *

UNITED STATES PATENT AND TRADEMARK OFFICE
CERTIFICATE OF CORRECTION

PATENT NO. : 4,279,593
DATED : July 21, 1981
INVENTOR(S) : Friedrich-Wilhelm Röhlcke It is certified that error appears in the above-identified patent and that said Letters Patent are hereby corrected as shown below:

Column 3, line 13, delete "wire supporting";

Signed and Sealed this

Twentieth Day of October 1981

[SEAL]

Attest:

GERALD J. MOSSINGHOFF

Attesting Officer  Commissioner of Patents and Trademarks